United States Patent
Linares

(10) Patent No.: US 8,764,837 B2
(45) Date of Patent: Jul. 1, 2014

(54) REINFORCED JOINT ASSEMBLY

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 757 days.

(21) Appl. No.: 12/411,149

(22) Filed: Mar. 25, 2009

(65) Prior Publication Data

US 2009/0248166 A1 Oct. 1, 2009

Related U.S. Application Data

(60) Provisional application No. 61/039,612, filed on Mar. 26, 2008.

(51) Int. Cl.
*A61F 2/30* (2006.01)

(52) U.S. Cl.
USPC .......... 623/20.14; 623/20.21; 623/20.28

(58) Field of Classification Search
CPC ......... A61F 2/30; A61F 2/389; A61F 2/3859; A61F 2/3886
USPC .......... 623/18.11, 20.14, 20.28, 20.33, 22.14, 623/19.12, 20.21, 20.22, 23.39, 23.4
See application file for complete search history.

(56) References Cited

U.S. PATENT DOCUMENTS

| | | |
|---|---|---|
| 2,667,644 A | 2/1954 | Johnson |
| 3,651,521 A | 3/1972 | Devas |
| 3,798,679 A | 3/1974 | Ewald |
| 3,875,594 A | 4/1975 | Swanson |
| 3,964,106 A | 6/1976 | Hutter, Jr. et al. |
| 4,215,439 A | 8/1980 | Gold et al. |
| 4,231,122 A | 11/1980 | Koeneman |
| 4,328,593 A | 5/1982 | Sutter et al. |
| 4,367,562 A | 1/1983 | Gauthier |
| 4,538,305 A | 9/1985 | Engelbrecht et al. |
| 4,714,477 A | 12/1987 | Fichera et al. |
| 4,950,298 A | 8/1990 | Gustilo et al. |
| 4,964,868 A | 10/1990 | Bloebaum |
| 4,990,161 A | 2/1991 | Kampner |
| 5,007,934 A | 4/1991 | Stone |
| 5,021,061 A | 6/1991 | Wevers et al. |
| 5,092,898 A | 3/1992 | Bekki et al. |
| 5,171,325 A | 12/1992 | Aulie |
| 5,197,987 A | 3/1993 | Koch et al. |
| 5,389,107 A | 2/1995 | Nassar et al. |
| 5,462,362 A | 10/1995 | Yuhta et al. |
| 5,509,934 A | 4/1996 | Cohen |

(Continued)

FOREIGN PATENT DOCUMENTS

JP 07116184 A 5/1995

*Primary Examiner* — Thomas J Sweet
*Assistant Examiner* — Christopher D Prone
(74) *Attorney, Agent, or Firm* — Gifford, Krass, Sprinkle, Anderson & Citkowski, P.C.; Douglas J. McEvoy

(57) ABSTRACT

A reinforced joint assembly includes a first implant portion secured to a sectioned end of a first bone. A second implant portion is likewise secured to a sectioned end of a second bone and in opposing fashion relative to the first implant to define a joint zone therebetween. The first implant exhibits a first surface profile, whereas the second implant exhibits a second and mating surface profile. A male projection extends from the first surface profile of the first implant and seats within a recess defined within the second implant.

8 Claims, 9 Drawing Sheets

(56) References Cited

U.S. PATENT DOCUMENTS

| | | | |
|---|---|---|---|
| 5,553,476 A | 9/1996 | Oehy et al. | |
| 5,571,193 A | 11/1996 | Kampner | |
| 5,593,445 A | 1/1997 | Waits | |
| 5,645,601 A | 7/1997 | Pope et al. | |
| 5,662,158 A | 9/1997 | Caldarise | |
| 5,676,702 A | 10/1997 | Ratron et al. | |
| 5,702,476 A | 12/1997 | Limacher et al. | |
| 5,728,175 A | 3/1998 | Rincoe | |
| 5,800,566 A | 9/1998 | Gramnas et al. | |
| 5,879,406 A | 3/1999 | Lilley | |
| 5,916,269 A * | 6/1999 | Serbousek et al. | 623/22.24 |
| 5,921,358 A | 7/1999 | Gramnas et al. | |
| 6,045,581 A | 4/2000 | Burkinshaw | |
| 6,165,223 A | 12/2000 | Metzger et al. | |
| 6,398,815 B1 | 6/2002 | Pope et al. | |
| 6,627,141 B2 | 9/2003 | McNulty et al. | |
| 6,660,040 B2 | 12/2003 | Chan et al. | |
| 6,692,679 B1 | 2/2004 | McNulty et al. | |
| 6,723,102 B2 | 4/2004 | Johnson et al. | |
| 6,800,298 B1 | 10/2004 | Burdick et al. | |
| 6,800,670 B2 | 10/2004 | Shen et al. | |
| 6,811,568 B2 | 11/2004 | Minamikawa | |
| 6,818,172 B2 | 11/2004 | King et al. | |
| 6,866,685 B2 | 3/2005 | Chan et al. | |
| 6,962,607 B2 | 11/2005 | Gundlapalli et al. | |
| 7,044,983 B1 | 5/2006 | Cheng et al. | |
| 7,066,958 B2 | 6/2006 | Ferree | |
| 7,077,867 B1 | 7/2006 | Pope et al. | |
| 7,087,091 B1 | 8/2006 | Chen et al. | |
| 7,109,181 B2 | 9/2006 | Cowlen et al. | |
| 7,148,209 B2 | 12/2006 | Hoemann et al. | |
| 7,175,666 B2 | 2/2007 | Yao | |
| 7,179,298 B2 | 2/2007 | Greenlee | |
| 7,186,364 B2 | 3/2007 | King et al. | |
| 7,331,995 B2 | 2/2008 | Eisermann et al. | |
| 7,384,430 B2 | 6/2008 | Greer et al. | |
| 7,578,851 B2 | 8/2009 | Dong et al. | |
| 7,771,485 B2 | 8/2010 | Grundei | |
| 7,780,738 B2 | 8/2010 | Khandkar et al. | |
| 2002/0183845 A1 | 12/2002 | Mansmann | |
| 2003/0065401 A1 * | 4/2003 | Amrich et al. | 623/23.55 |
| 2003/0114935 A1 | 6/2003 | Chan et al. | |
| 2003/0216669 A1 | 11/2003 | Lang et al. | |
| 2004/0024460 A1 | 2/2004 | Ferree | |
| 2004/0068322 A1 | 4/2004 | Ferree | |
| 2005/0055100 A1 | 3/2005 | Lewis et al. | |
| 2005/0171604 A1 | 8/2005 | Michalow | |
| 2005/0192672 A1 | 9/2005 | Wyss et al. | |
| 2005/0192674 A1 | 9/2005 | Ferree | |
| 2005/0287187 A1 | 12/2005 | Mansmann | |
| 2006/0015186 A1 | 1/2006 | Isaac | |
| 2007/0179613 A1 | 8/2007 | Heinz | |
| 2007/0287027 A1 | 12/2007 | Justin et al. | |
| 2008/0033567 A1 | 2/2008 | Stchur | |
| 2008/0288081 A1 * | 11/2008 | Scrafton et al. | 623/20.33 |
| 2009/0076605 A1 | 3/2009 | Linares | |
| 2009/0125108 A1 | 5/2009 | Linares | |

\* cited by examiner

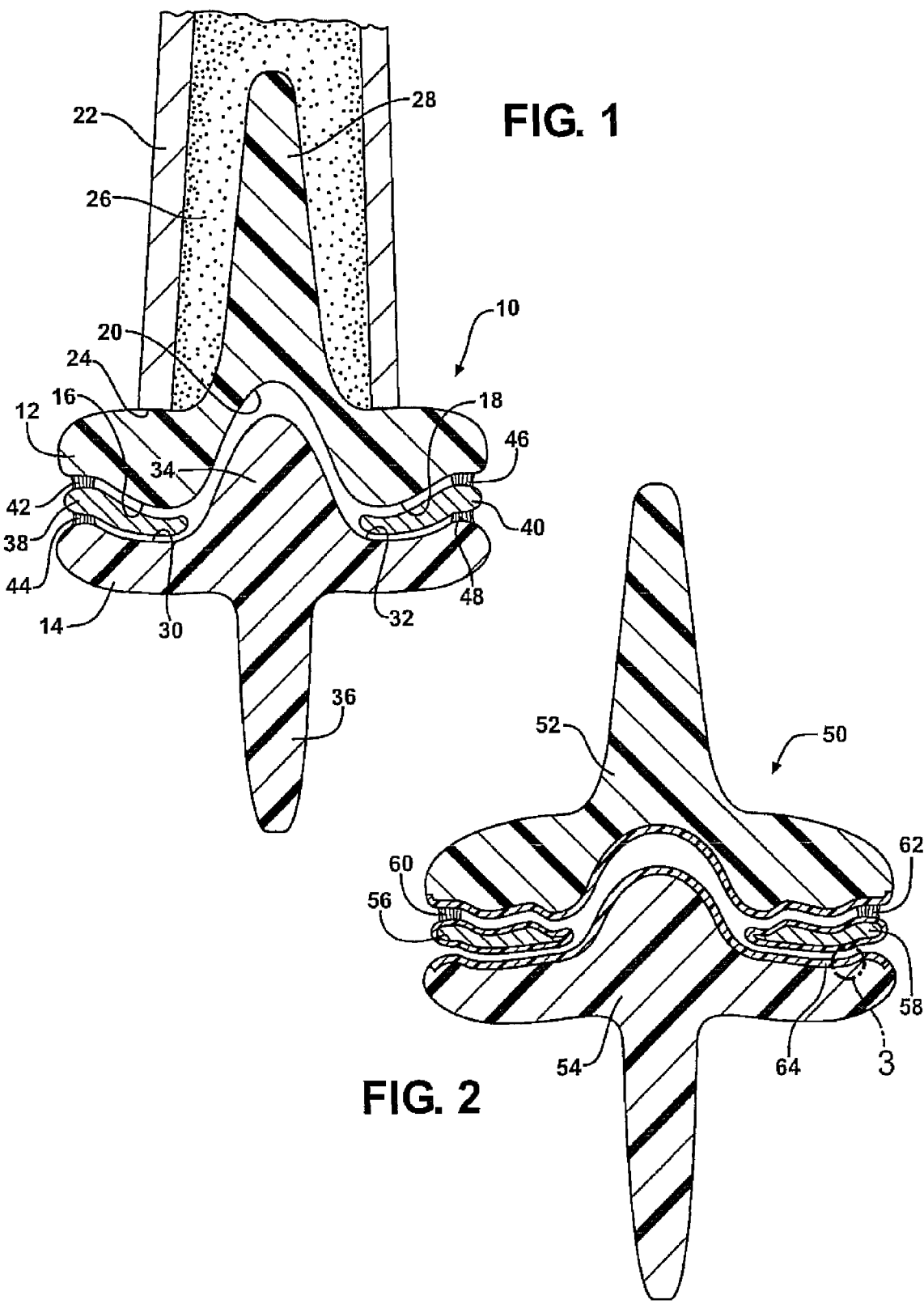

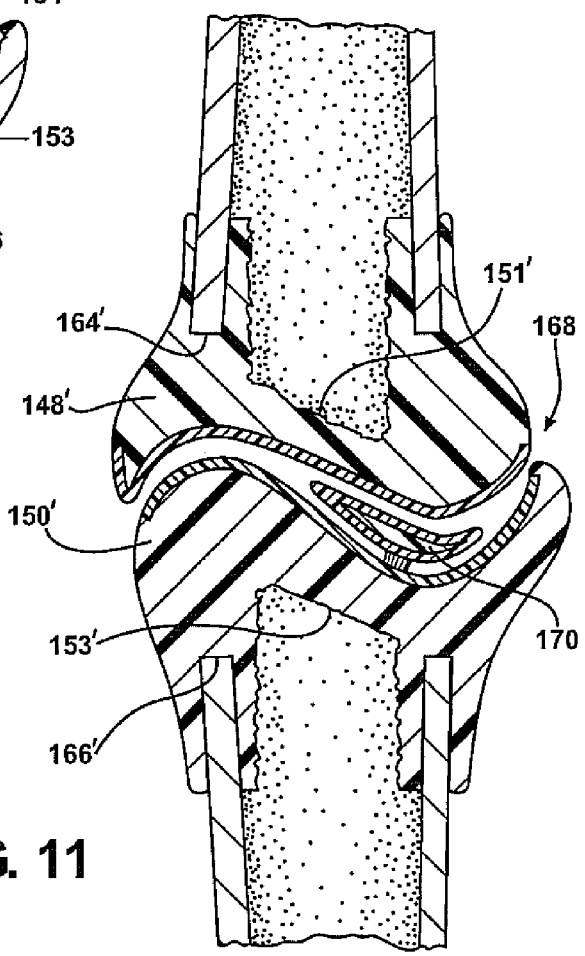

REINFORCED JOINT ASSEMBLY

CROSS-REFERENCE TO RELATED APPLICATIONS

The present application claims the priority of U.S. provisional application Ser. No. 61/039,612, filed Mar. 26, 2008, for a Joint Construction, Such as for Use by Athletes.

FIELD OF THE INVENTION

The present invention relates generally to artificial joint constructions. More specifically, the present invention discloses a heavy duty and reinforced joint construction for use such as by athletes and which exhibits increased wear resistance, durability and load tolerances.

BACKGROUND OF THE INVENTION

Artificial joint constructions are known in the art prior art. Such joint constructions are often provided as a replacement for worn out knee, elbow, hip and other known joint assemblies. It is also known that, given active lifestyles, replacement joint assemblies are also known for individuals exhibiting fairly active lifestyles and for which prior art joints of limited motion and durability are a shortcoming.

SUMMARY OF THE INVENTION

The present invention discloses a heavy duty and reinforced joint construction, such as for use by athletes, and which provides increased range and durability over prior art artificial joint assemblies. The reinforced joint construction includes a first implant portion secured to a sectioned end of a first bone. A second implant portion is likewise secured to a sectioned end of a second bone and in opposing fashion relative to the first implant to define a joint zone therebetween. The first implant exhibits a first surface profile, whereas the second implant exhibits a second and mating surface profile. A male projection of desired shape and configuration extends from the first surface profile of the first implant and seats within a substantially mating recess configuration defined within an opposing surface of the second implant.

Additional features include at least one inter-disposed and supporting portion in contact with the first and second surface profiles and which provides additional cushioning and biasing support to the joint assembly. First and second cartilage surfaced and supporting portions are further established between the mating surface profiles and contribute towards maintaining the integrity of the joint assembly.

A softened and lubricated plastic surface is applied upon at least one of the mating surface profiles and the male projection. At least one of the softened plastic surfaces further includes a lubricant supporting pattern exhibiting crosswise extending and fluid retaining tracks. The cartilage surfaced and supporting portions further partially overlap one another in position between the mating surface profiles and assist in providing an enhanced degree of substantially frictionless and lubricating support to the reinforced joint assembly.

Each of the implants exhibits a peripheral extending and undercut profile for securing to an associated and sectioned bone end. Each of the implants can further include a roughened inner surface for promoting bone marrow adhesion and to prevent inadvertent separation of the end joint from the bone (natural or artificial). Additional features include at least one pin for providing additional securing the implant profile to the sectioned bone end.

As shown in further variants, the male implant extending portion can also extend in an angled fashion and seat within a likewise angled female inner recess. In a yet further variant, a first implant portion establishes an outer annular seating location about its periphery with respect to a second opposing implant portion.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a plan cutaway view of a reinforced joint assembly according to a first preferred embodiment and including multiple joint contacting and fused cartilage force absorbing locations established between first and second bone mounted implants;

FIG. 2 is a modified view of the reinforced joint assembly of FIG. 1 and illustrating lubricant retaining grid patterns arrayed on the multiple opposing surfaces between the opposing implants and intermediately positioned fused cartilage portions;

FIG. 10 is a succeeding illustration of a joint assembly incorporating two sectioned end bone mounted implants and exhibiting first and second interdisposed and fused cartilage support portions;

FIG. 11 is slightly varied assembly in comparison to that shown in FIG. 10 and illustrating a single centrally supporting and fused cartilage support portion;

DETAILED DESCRIPTION OF THE PREFERRED EMBODIMENTS

Figure 3:
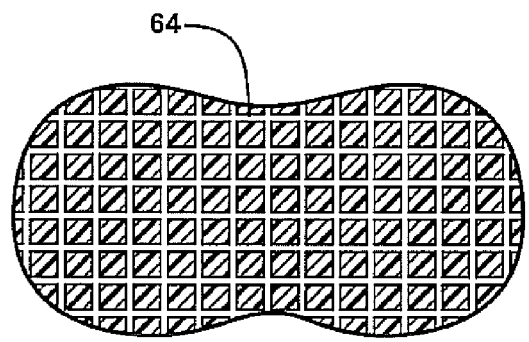
FIG. 3 is a sectional plan view of a selected fluid retaining grid surface pattern associated with an opposing implant.

Referring now to FIG. 1, a plan cutaway view is shown at 10 of a reinforced joint assembly according to a first preferred embodiment. As previously described, the present invention discloses a heavy duty and reinforced joint construction for use such as by athletes, and which exhibits increased wear resistance, durability and load tolerances.

While not evident from the various cutaway illustrations referenced herein, a number of the heavy duty/reinforced joint assemblies can include the male implant portion exhibiting a more pronounced configuration and which can be more effectively and completely seated within a female receiver such that additional force absorbing characteristics are established for holding together the super joint thus created. Also, the illustrations shown herein are primarily in two dimensional cutaway, it being understood that the configuration of the male and female implants in three dimension typically exhibiting more pronounced ball and socket style engagement configurations, these contributing not only to the super duty engaging and impact absorbing properties of the joint assemblies, but also to the universal range of pivoting established between the male and female portions and as will be further described herein.

Referring again to FIG. 1, the cutaway shown is of first 12 and second 14 hard plastic end mounted implants, these collectively defining a joint region selected from any including knee, elbow, lip, wrist, ankle or other joint and which can benefit from a more durable construction associated with repetitive athletic activities. The first implant 12, in the instance of the illustration being a female receiver, exhibits a outwardly arrayed surface including outer perimeter defined and arcuate surfaces 16 and 18, as well as a generally centralized and inner-most recessed cavity 20.

The female implant 12 is mounted within a sectioned end of an existing bone 22, and which includes an outermost extending sectioned edge 24 and an open interior such as which is filled with an inner bone marrow 26. The female implant 12 further exhibits a pronounced and rearwardly/inwardly extending profile, see at 28, this seating within the section bone interior (and embedded within the marrow 26) to provide additional seating and adhering surface area for retaining the female implant 12 at its seated location relative the sectioned bone end.

According to one non-limiting embodiment, such implant assemblies contemplate removing a previously worn away or damaged section of a user's joint structure, such as by sawing or machining the damaged end from an existing bone in situ within the patient, and prior to installation of new synthetic/prosthetic implant portions. Further, and while it is preferable that the natural bonding action of the bone marrow be employed for securing the inserting profile 28 of the implant portion 12, other and additional embodiments will also discuss the ability to use pins, fasteners, injected plastic adhesives, cements and the like for assisting in bonding the specified implant to a sectioned end of the bone.

The second or male implant, again at 14, further includes each of mating outer perimeter surfaces 30 and 32 (these mating with the configuration of the first implant surfaces 16 and 18 of the female implant 12 as best shown in the plan cutaway in FIG. 1). The male implant 14 also exhibits a central projecting and seating portion 34, and which is further dimensioned so as to seat within the inner cavity 20. The second implant 14 also includes an opposite and rearward extending profile 36 for securing within a second sectioned bone end (not shown) and in substantially the same fashion as shown in reference to the inserting profile 28 associated with the female implant 12.

Also shown in FIG. 1 are multiple joint contacting and fused bone or cartilage force absorbing portions, see at 38 and 40, these being established at opposing joint surface locations established between the first 12 and second 14 bone mounted implants. The cartilage portions 38 and 40 can also constitute a bone-like material mimicking that associated with each of the implant bodies 12 and 14, and which establish additional joint support which can further be fused at outer locations 42 & 44 (with respect to cartilage portion 38) and at 46 & 48 (for cartilage portion 40). As will be further described in reference to the several additional variants, the fused locations can be arranged at any of inner, outer or intermediate locations relative to the periphery of the established joint structure, and depending upon the desired performance characteristics which the joint assembly is attempting to replicate.

The functioning of the cartilage portions is such that they provide additional contacting and load/force bearing surfaces within the joint zone and between the implants 12 and 14, and such as which is not provided for by existing artificial joint assemblies. Also not shown in FIG. 1, but evident throughout several of the additional illustrations, is the provision of soft plastic lubricating surfaces between the opposing faces of the bone and/or cartilage defined portions, as well as the provision of natural or artificial lubricants for enhancing the frictionless operation of the joint.

Referring now to FIG. 2, a modified view is shown at 50 of a reinforced joint assembly similar in construction to that illustrated in FIG. 1, but not showing the sectioned bones to which the implants, see first implant 52 and second 54 opposing arrayed implant, are secured. Similar additional and intervening cartilage supporting (e.g. bone-like) portions are shown at 56 and 58, these similar to those previously shown at 38 and 40 in FIG. 1, and with the exception that a single pair of fused locations 60 and 62 are provided for securing the portions 56 and 58 to only the upper female or first implant 52, and while permitting the lower (male) implant a range of independent motion, it being further understood that such an arrangement can be reversed, and so that the cartilage portions are fused only to the mail implant 54.

Also incorporated into the implant assembly 50 is the provision of a number of soft plastic exposed surfaces, and which are further disclosed as lubricant retaining grid patterns as also shown at 64 in the enlarged partial view of FIG. 3. The exposed surfaces may be defined on each opposing face of implants 52 and 54, as well as the intermediately positioned cartilage portions 56 and 58. In this fashion, the soft plastic and frictionless promoting surfaces can be arrayed on the multiple opposing surfaces between the opposing implants and intermediately positioned fused cartilage portions.

Referencing again FIG. 3, the sectional plan view shown is of a selected fluid retaining grid surface pattern 64 associated with an implant or intermediately positioned synthetic (again faux bone or cartilage) portion. As shown a plurality of cross wise extending tracks or grooves, of selected dimension, are defined in the exposed surface of the grid defined pattern 64 and facilitate the location and retention of lubricant for maximizing the efficiency of the joint implant. It is also envisioned that other grid surface patterns or configuration can be employed with the lubricant inducing/soft plastic surfaces.

Figure 4:
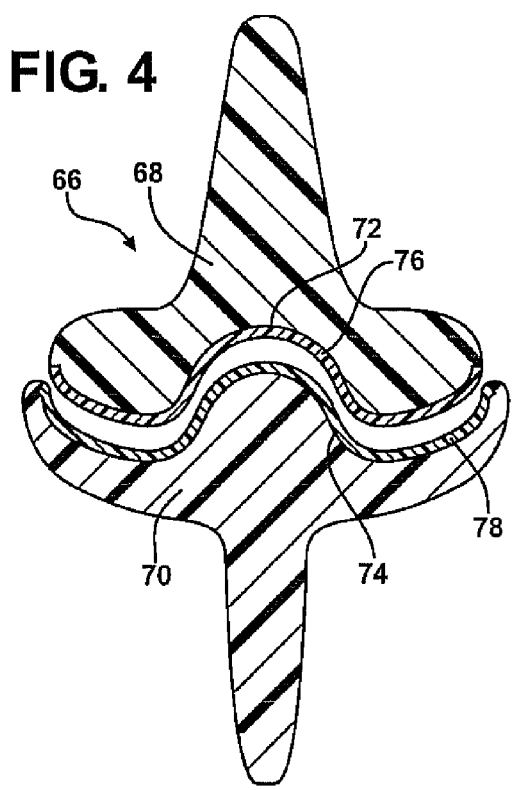
FIG. 4 is a modified cutaway of a reinforced joint assembly according to a further preferred embodiment and illustrating first and second opposing implants exhibiting a different center configuration with pronounced male and female ball and receiver portions.

Referring now to FIG. 4, a modified cutaway is shown at 66 of a reinforced joint assembly according to a further preferred embodiment and illustrating first 68 and second 70 opposing implants. These exhibit a first example of a mating center configuration, see surface pattern 72 for implant 68 and at 74 for implant 70. The surface patterns generally define therebetween pronounced (e.g. more rounded) male and female ball and receiver portions. Also disclosed is the provision of soft plastic surface (e.g. cartilage wearing or substitute) portions, see at 76 and 78, the purpose for which is again to maximize both the effective seating area and support of the male and female portions.

Figure 5:
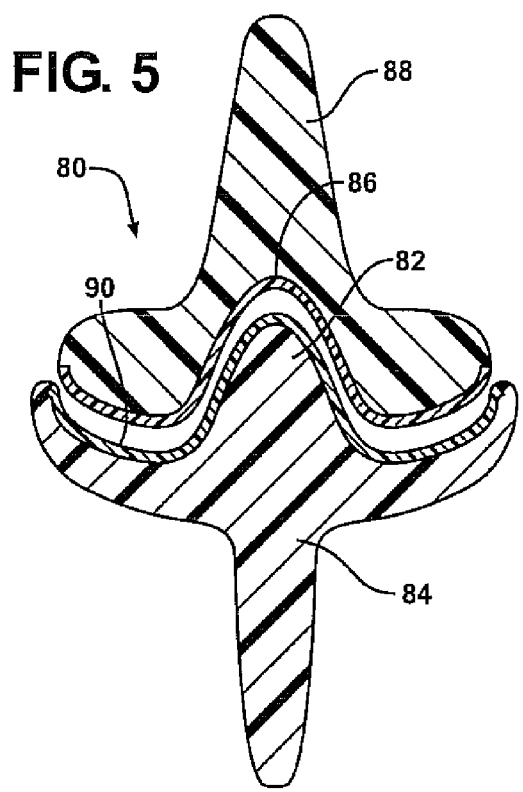
FIG. 5 is a further modified implant configuration with a more pronounced center support established between first and second implant.
Figure 5A:
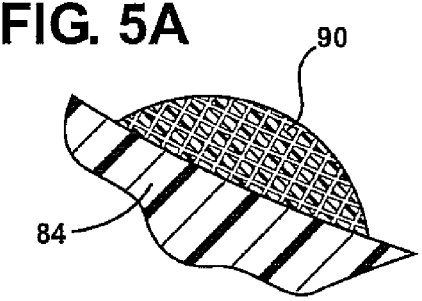
FIG. 5A is a partial illustration of a lubricant track supporting surface associated with an implant surface in FIG. 5.

As further shown in FIG. 5 at 80, a further modified implant configuration (such as in comparison to FIG. 4) is illustrated and which exhibits an even more pronounced center support, see generally more conical influenced male portion at 82 and which is associated with selected implant 84, this established in opposing fashion with a center receiver location 86 defining a portion of a second (female) implant 88. The provision of softened plastic and lubricant retaining track channels is again shown at 90 (see also FIG. 5A which is a partial illustration of a lubricant track supporting surface associated with an implant surface in FIG. 5).

Figure 6:
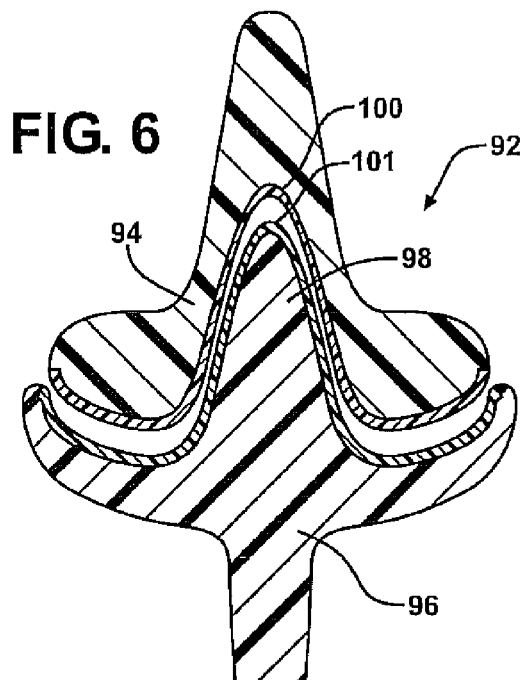
FIG. 6 is a yet further modified implant configuration with first and second opposing joint defining implants exhibiting a further increased male/receiver socket configuration.
Figure 7:
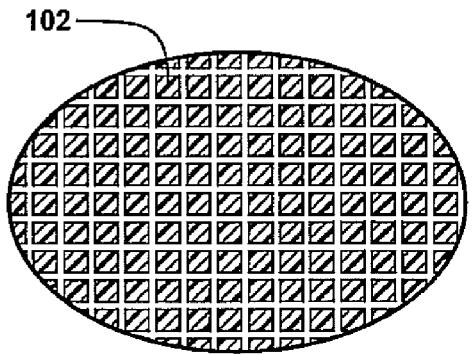
FIG. 7 is an illustration similar to that previously shown in FIG. 3 of a fluid retaining grid including crosswise extending tracks and which is exhibited upon an opposing soft plastic cartilage surface of a selected implant.

As further shown in FIG. 6, a yet further modified implant configuration 92 illustrates first (female) 94 and second (male) 96 opposing joint defining implants exhibiting a further increased male/receiver socket configuration. This includes a lengthened center seating portion 98, associated with the implant 98, and which seats within a further recessed and likewise mating receiver location 100 defined within the associated, e.g. composite hard plastic, body of the implant 94. As again shown, the provision of a composite soft plastic covering (see at 100 for female implant 94 and further at 101 for male implant 96) can be applied to both opposing surface profiles of the implants 94 and 96. FIG. 7 is an illustration similar to that previously shown in FIG. 3 of a fluid retaining grid 102 and which again includes crosswise extending tracks which are exhibited upon an opposing soft plastic cartilage surface of a selected implant, these again further assisting in the distribution and retention of lubricant patterns to extend the wear life of the joint.

Figure 8:
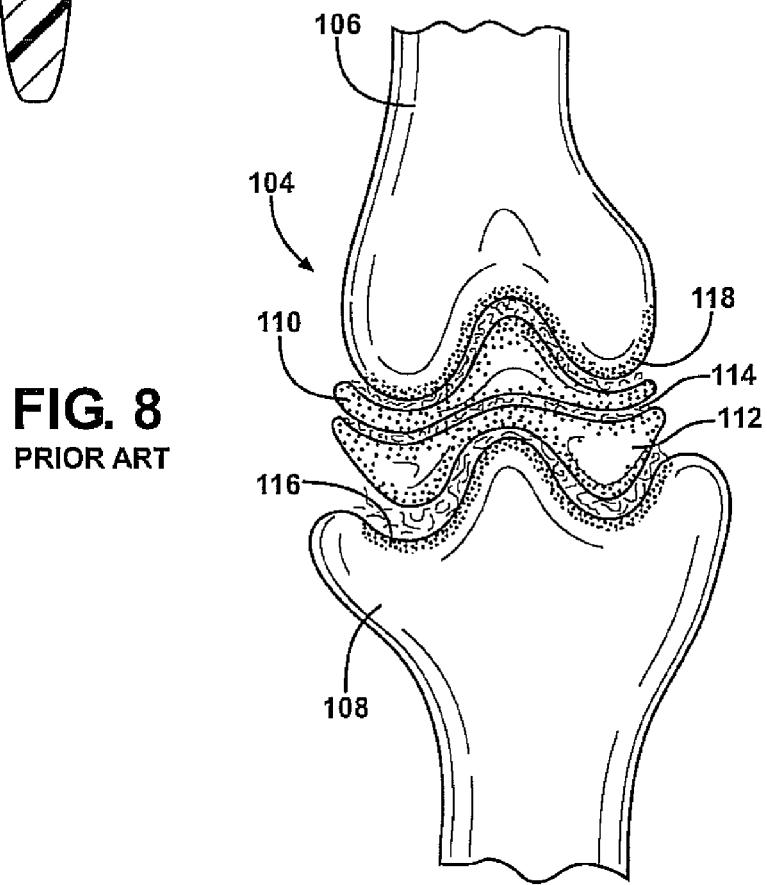
FIG. 8 is a prior art illustration of a horse bone structure and illustrating its multiple bone cartilage and interstitial fluid structure.

Referring now to FIG. 8, a prior art illustration is generally shown at 104 of a conventional horse bone/joint structure including upper 106 and lower 108 bones. Also illustrated are multiple bone portions, see at 110 and 112, in addition to interstitial fluid structure 114 and soft plastic cartilage support portions 116 and 118.

Figure 9:
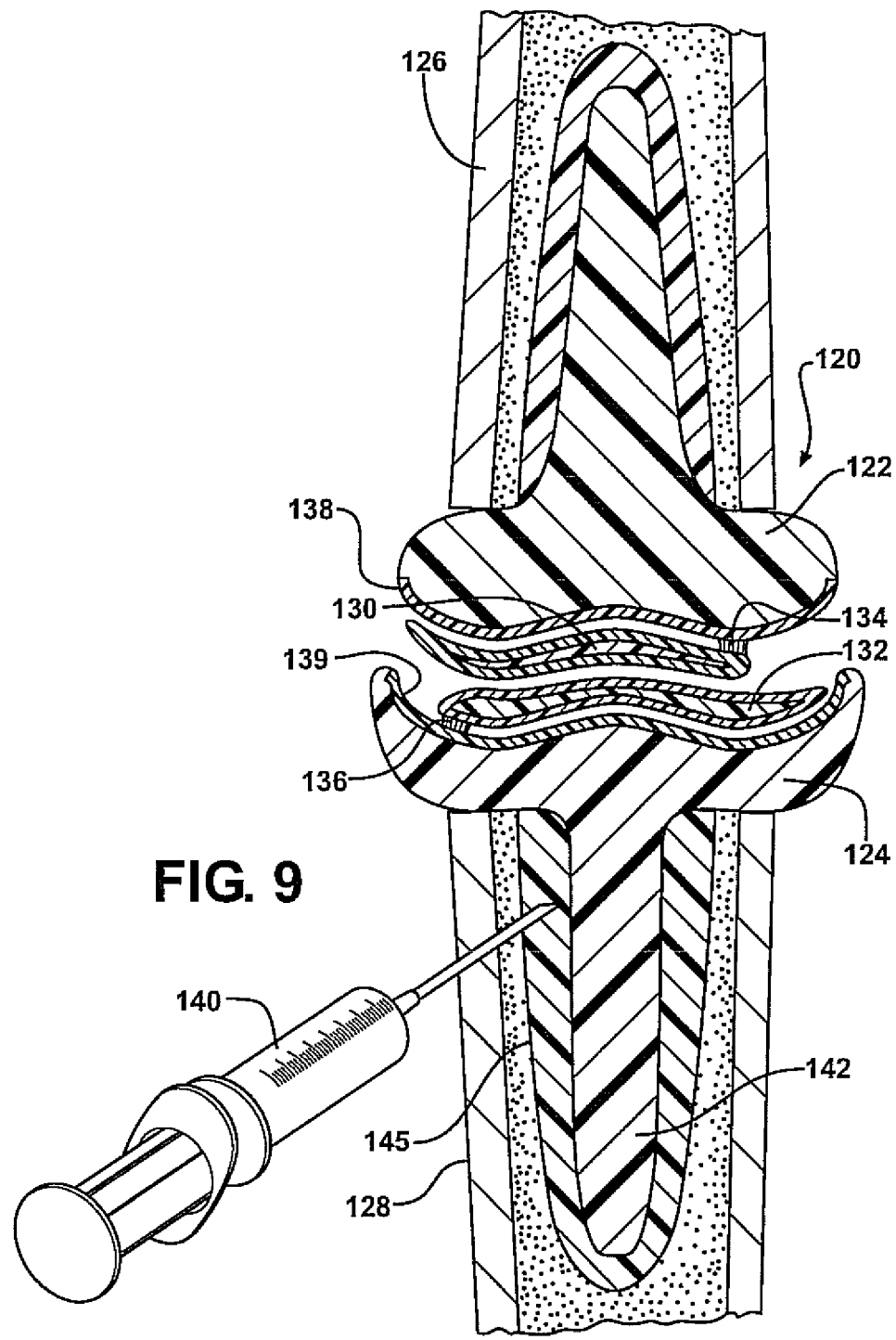
FIG. 9 is a cutaway illustration of a reinforced implant scenario replicating that shown in FIG. 8 and which includes first and second sectioned bone-end installed implants and with fused inter-disposed cartilage portions.

The purpose of FIG. 8 is to illustrate the operation of a horse joint structure and to equate that to a suitable reinforced artificial human implant, as further shown at 120 in the cutaway illustration of FIG. 9. The assembly 120 includes first 122 and second 124 sectioned bone-end installed implants (see as further attached to sectioned bones 126 and 128). Again shown are inter-disposed bone portions 130 and 132, these being fused at locations 134 and 136 respectively, to joint surface locations of the bones 122 and 124. The provision of (composite) soft plastic cartilage surfaces is again shown at 138 and 139 for joint implants 122 and 124, respectively and, in cooperation with the (composite) hardened plastic construction of the implants, attempts to duplicate the reinforcing and wear resistant aspects of the equine bone structure of FIG. 8, and such as further establishes a total of six (6) cartilage absorbing surfaces between the implants 122 and 124.

Also referenced in FIG. 9 is the provision of an injectable liquid plastic, see syringe 140, and which is provided in use with each of the inner bone structures (see bone 128). Each implant includes a reverse extending mounting support (see at 142 for selected implant 124). Flexible membranes, illustrated as plastic bags 144 and 145, is pre-inserted into the associated and marrow filled cavity of the selected bone 128 and prior to the installation of the associated implant 124. At this point, a volume of the liquid plastic is injected between the inner implant extending support 142 and the bag/fluid impervious membrane 144. This causes the membrane to deflect outwardly (see arrows) and, upon setting and hardening, to permanently bond the implant to the bone.

FIGS. 10-13 illustrated a series of modified and related joint assemblies, and in which first and second composite implants each exhibit undercut peripheral surfaces which are dimensioned to secure to sectioned bone ends. As first shown in FIG. 10 joint assembly 146 incorporates two sectioned end bone mounted implants 148 and 150. The implants 148 and 150 exhibit interior profiles 151 and 153 communicating with the bone interior, the implants further exhibiting first 152 and second 154 cartilage surfaced and supporting portions which are inter-disposed and fused, at 156 and 158.

The implants 148 and 150 are mounted to existing sectioned bone end locations, see bones 160 and 162, such as again by undercut machined and inwardly facing edge profiles, see at 164 and 166 defined within each of the implants 148 and 150. In this fashion, the implants are dimensioned to correlate to a given bone diameter and, prior to installation, are machined to precisely fit in securing fashion to the sectioned bone ends. Further, the provision of inner marrow (see at 165 and 167 for bones 160 and 612, respectively) for contacting and gripping the inner defined implant profiles 151 and 153 associated with each bone functions to assist in bonding the implants in their installed bone end locations.

Figure 12:
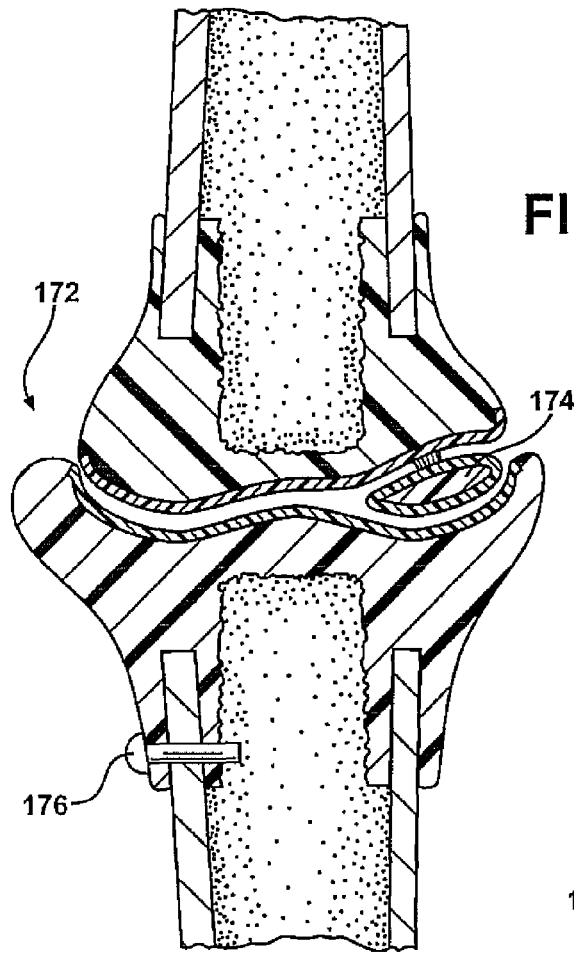
FIG. 12 is a further variant with a single cartilage support and in which the implants are secured by pins to sectioned bone end locations.
Figure 13:
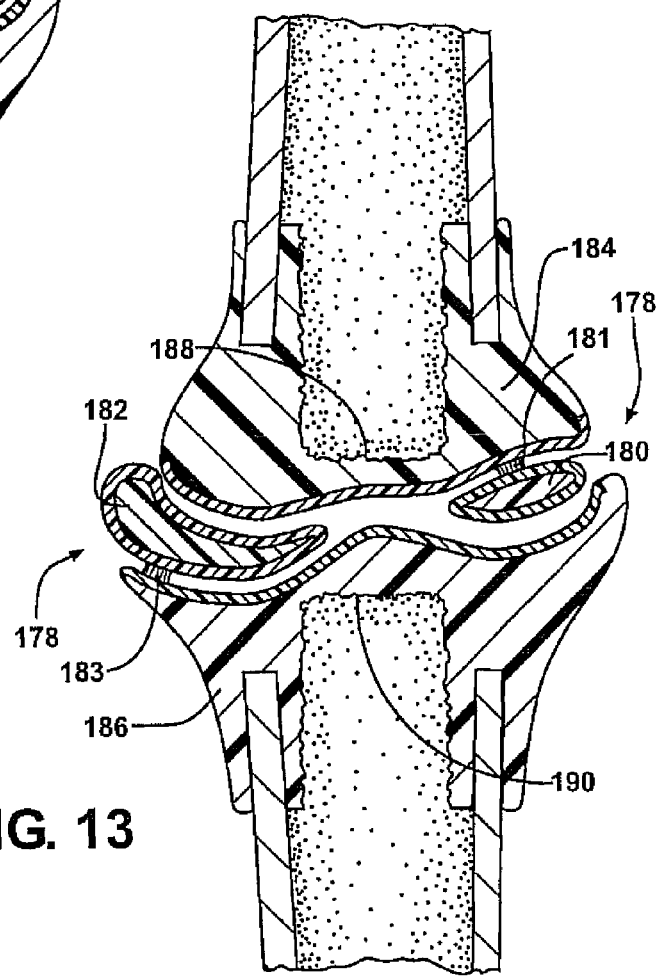
FIG. 13 is a yet further modified variant as compared to FIG. 12 and in which first and second interspaced and fused cartilage portions are arranged on opposite sides of an implant defined zone.

Without repeating in detail each corresponding feature presented in each of FIGS. 11-13, FIG. 11 is a slightly varied assembly 168 in comparison to that shown in FIG. 10 and illustrates modified implant portions 148' and 150', these generally including a single centrally supporting and fused support portion, see further at 170 and which is connected to a surface locations of the portion 150'. The provision of a single and central disposed support (and cartilage surfaced) portion 170 is intended to provide buttressing support at a location in which excessive joint wear may otherwise occur and without the need for a pair of inter-disposed supports as in earlier variants. Additional features such as the undercut portions 164' and 166' defined in the inner facing annular surfaces of the implants, as well as the inner bone facing profiles (at 151' and 153')

FIG. 12 illustrates a further variant 172 similar in respects to that illustrated in FIG. 11 with modified joint surface profile, and with a single cartilage surface support 174 likewise fused at an interior location of a selected upper implant. The implants can further be secured by pins, see at 176, to sectioned bone end locations. As shown, a cement material can additionally or alternatively be used to secure the implant to the sectioned bone end.

FIG. 13 illustrates at 178 a yet further modified variant as compared to FIG. 12 and in which first 180 and second 182 interspaced and fused cartilage portions (see fused locations 181 and 183, respectively for securing cartilage portion 180 to surface location of first implant 184 and further for securing cartilage portion 182 to opposite edge surface location of second implant 186) these arranged on opposite sides of an implant defined zone. As further particularly shown, the under surface profile associated with each implant 184 and 186 can be textured, or roughened, as shown at 188 and 190, in order to provide additional gripping surface area to which the inner defined volumes of bone marrow can exert greater bonding and gripping of the sectioned bone end installed implants. Other features, such as the undercut portions are illustrated in similar fashion as shown in FIGS. 11 and 12.

Figure 14:
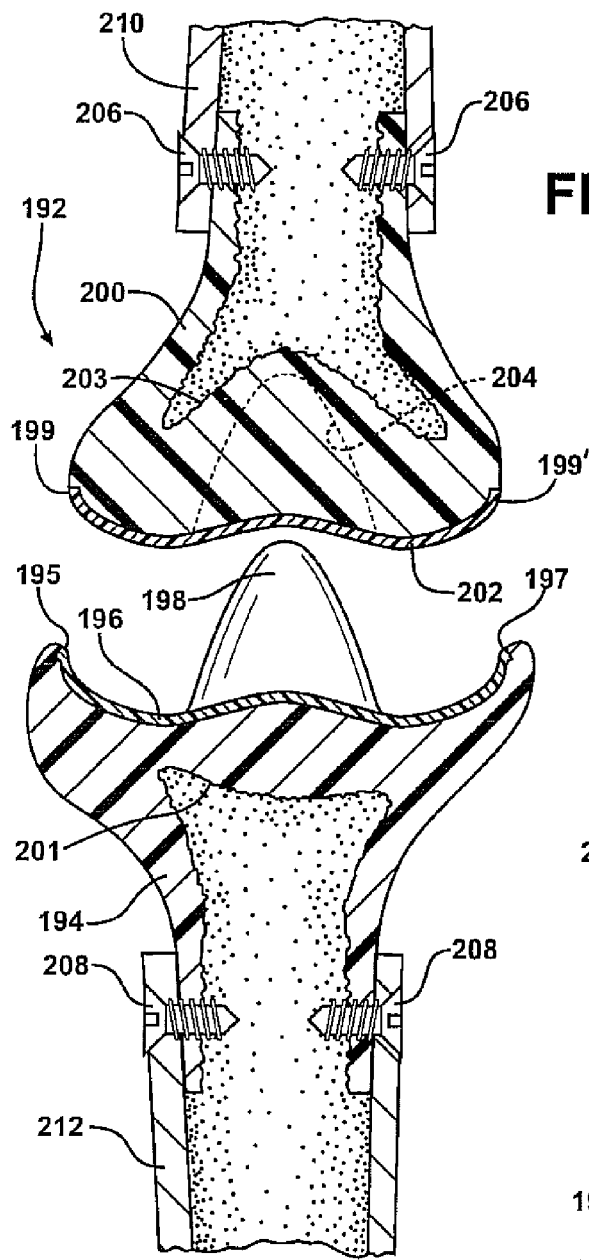
FIG. 14 is an exploded front view of a modified knee joint implant assembly in which a first lower bone secured plastic implant exhibits a first surface profile with a central and conical upward projecting male portion, a second upper and opposing arrayed plastic implant exhibiting a second mating surface profile and a further recessed receiver location for seating the conical projecting male portion in a further secure and reinforcing engagement.

Referring now to FIG. 14, an exploded front view 192 is shown of a modified knee joint implant assembly in which a first lower bone secured (e.g. composite hardened plastic) implant 194 exhibits a first surface profile 196 and a central and conical upward projecting male portion 198. A second upper and opposing arrayed plastic implant 200 exhibits a second mating surface profile 202 and a further recessed receiver location 204 (see as shown in phantom) for receiving and seating the conical projecting male portion 198 in a further secure and reinforcing engagement.

As with previous embodiments, the opposing surface profiles of the joint implants are provided such as by a soft lubricant material and can further exhibit any desired mating configuration, this contributing to a desired performance profile of the joint. As shown in FIG. 14, the joint implant 194 illustrates upwardly angled perimeter edge locations (see at 195 and 197) which seat over and around associated rounded edges 199 and 199' of the upper located implant 200.

As in previous embodiments, composite softened plastic surfaces 196 and 202 are provided upon opposing surfaces of the mating profiles associated with the implants 194 and 200, as well as optionally provided upon the extending male portion 198. The implants 194 and 200 may again include roughened/textured inner defined surfaces (see at 201 and 203) for facilitating bonding of marrow, and can further be secured through the assistance of pins, see at 206 and 208, these being laterally mounted with respect to associated and sectioned bone ends 210 and 212.

Figure 15:
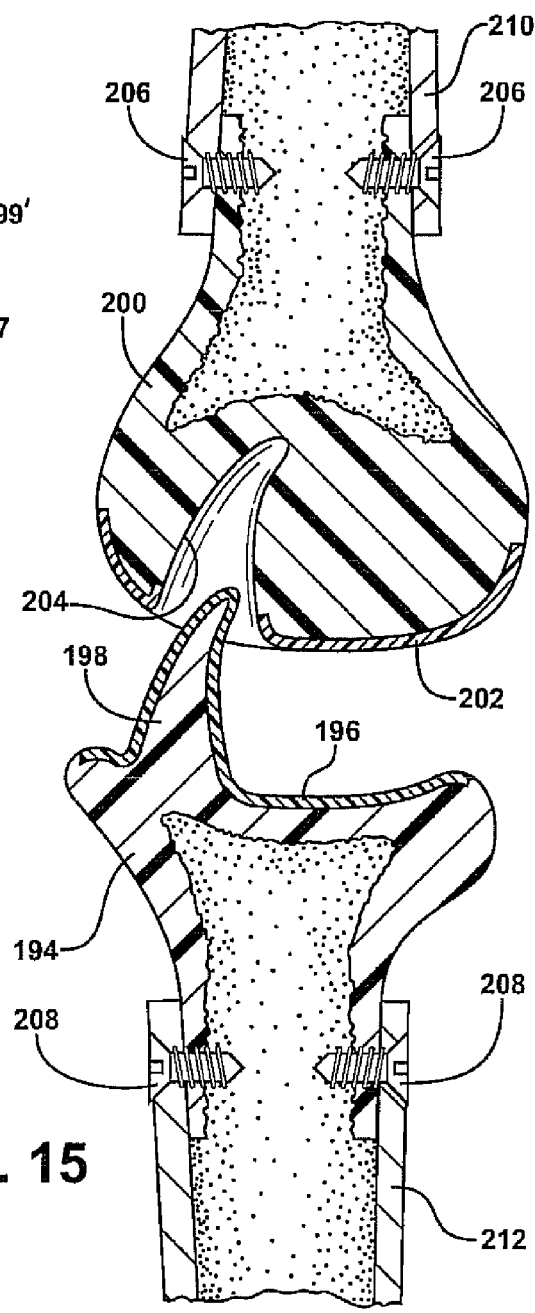
FIG. 15 is a rotated side view of FIG. 14 and better illustrating the male and receiver configuration associated with the first and second implants, and in particular the edge configured and angled seating profile for maximizing force absorption capabilities.
Figure 16:
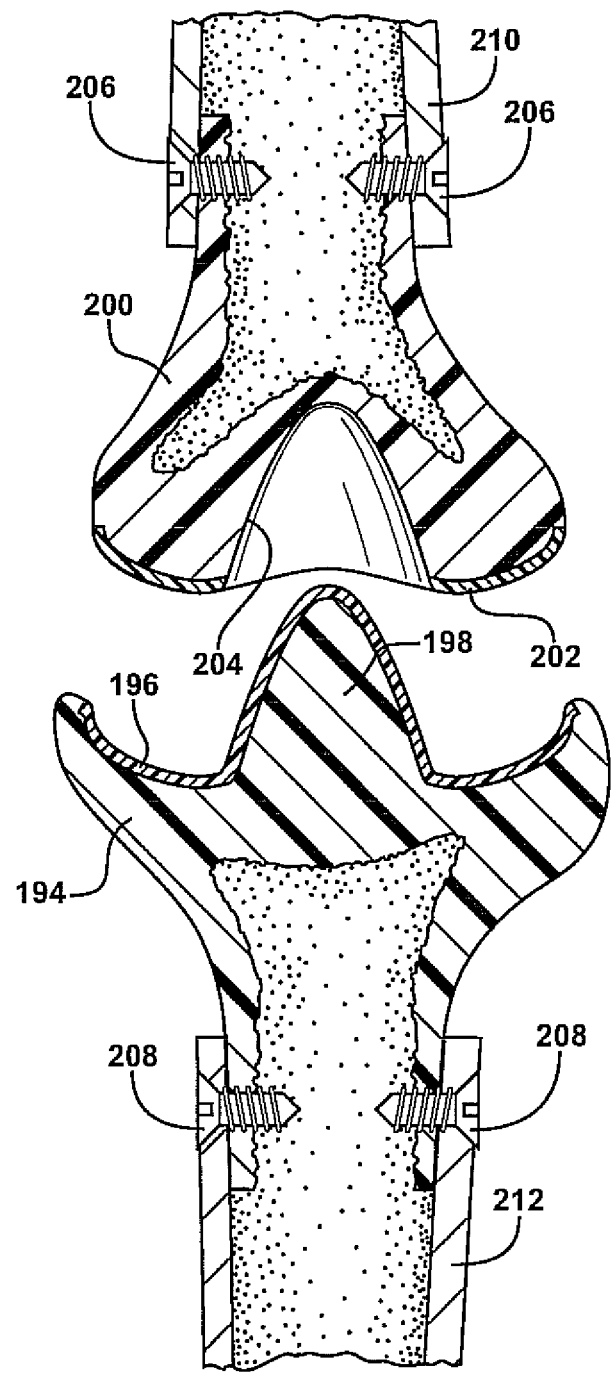
FIG. 16 is a further rotated rear view of the assembly shown in FIGS. 14 and 15.

FIG. 15 is a rotated side view of FIG. 14 and better illustrates the male and receiver configuration associated with the first lower 194 and second upper 200 implants. In particular, the edge configured and angled seating profile established between the male portion 198 and female receiver 204 and in combination with the normal opposing joint surfaces 196 and 202, is better shown from this angle for maximizing force absorption capabilities, such as during experiencing of increased forces associated with an athletic joint assembly. FIG. 16, a further rotated rear view of the assembly shown in FIGS. 14 and 15 and repeats the same elements previously described from a further rotated position.

Figure 17:
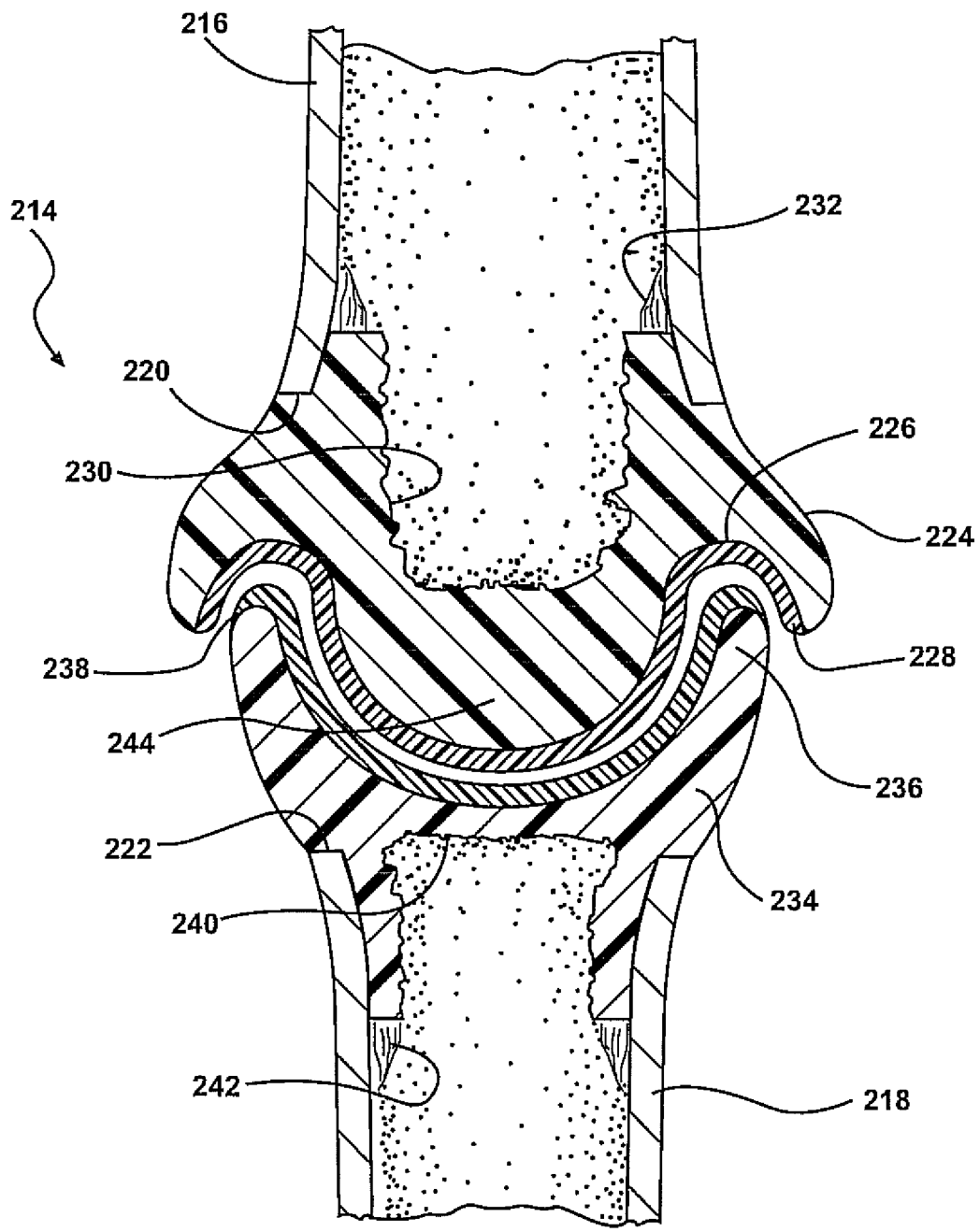
FIG. 17 is a final cutaway plan view of a reinforced joint assembly and in which a first implant portion establishes an outer annular seating location about its periphery with respect to a second opposing implant portion.

Finally, and referring to FIG. 17, illustrated at 214 is a cutaway plan view of a reinforced joint assembly employed in such as a heavy duty knee application between upper 216 and lower 218 bones, each of which including sectioned ends which are defined at 220 and 222. A first or upper implant portion is shown at 224 and again can be constructed from such as a plastic, composite plastic or even metallic/composite material and which establishes an outer annular curved seating location (see modified and arcuate "U" shape outer configuration at 226) about its periphery. The upper implant 224 again includes other features common to many of the previously described variants, these including a soft plastic exterior facing surface 228, as well as a roughened inner surface 230 which facilitates contact with the inner bone defined marrow. As also shown at 232, natural bone growth is promoted by the marrow between the outer connecting periphery of the implant 216 and the connecting edge 220 of the bone.

A second or lower implant 234 is similarly attached to the sectioned end 22 of the bone 218 and defines an inwardly spaced and seating outer perimeter, see at 236. The extending perimeter location 236 is seated within a generally trough location associated with the seating location 226 associated with the upper and outwardly dimensioned implant 224. The lower implant 234 again includes an opposing soft plastic cartilage layer 238, as well as roughened inner bone marrow adhering surface 240 and bone growth promoting location 242 defined between the bone 218 and the inserting location of the implant 234.

As with earlier embodiments, an associated male projection is represented at 244 with regard to the upper implant 224 and which can seat within a mating and opposing centrally recessed configuration associated with the lower implant 234. The construction of the implants are further such that the opposing cartilage layers 228 and 238 define enhanced frictionless and wear resistant layers associated with the artificial implant portions to an enhanced degree consistent with providing an athletic-type reinforced joint assembly.

The joint assembly 214 exhibits another possible configuration and by which the lower implant 234 can pivot and/or rotate within the upper outer dimensioned implant 224, further without risk of the joint implants becoming disengaged. This feature is of further importance when it is considered that, during joint replacement, the natural ligaments are often severed, usually permanently, and which can otherwise result in the subsequently installed implant portions becoming detached relative to one another in less robust assemblies. It is also envisioned that the arrangement established by the implants 224 and 234 can be reversed, and such as with the lower implant defining the outwardly displaced and peripheral seating portion relative to an inwardly dimensioned upper implant portion.

As with the several preceding variants, the existence of additional ligaments or other retaining structure is not shown, however is understood to exist in some or all of the variants and in order to facilitate retaining a given joint structure in a desired spacing and mating arrangement. It is also understood that the opposing implant configurations can be reconfigured in any fashion which will facilitate providing increased or reinforced impact or load absorbing properties for a selected joint assembly, including those for a knee, elbow, shoulder, ankle or the like.

Having described my invention, other and additional preferred embodiments will become apparent to those skilled in the art to which it pertains, and without deviating from the scope of the appended claims:

I claim:

1. A reinforced joint assembly, comprising:
   a first implant adapted to being a secured to a sectioned end of a first bone;
   a second implant adapted to being secured to a sectioned end of a second bone in opposing fashion to said first implant to define a joint zone therebetween;
   said first implant having a first surface profile and said second implant having a second surface profile, each of said surface profiles including multiple peaks and valleys which are contoured so as to mate with each other, each of said surface profiles further including a softened plastic;

a first tear drop shaped cartilage portion arranged at a first location between said first and second surface profiles, a first plurality of short strands being bunched together and connecting said first cartilage portion to said first surface profile; and a second tear drop shaped cartilage portion arranged at a second location between said second and first surface profiles, a further plurality of short strands being bunched together and connecting said second cartilage portion said second surface profile, said cartilage portions each establishing multiple wear surfaces on opposite sides thereof and permitted by said bunched connecting strands a limited range of inter-displaceable contact with each of said first and second implant surface profiles.

2. The joint assembly as described in claim 1, at least one of said softened plastic surfaces further comprising a fluid lubricant grid pattern having crosswise extending and fluid retaining tracks.

3. The joint assembly as described in claim 1, further comprising each of said implants having a peripheral extending and undercut profile for securing to an associated and sectioned bone end.

4. The joint assembly as described in claim 1, each of said implants further comprising a roughened inner surface for promoting bone marrow adhesion.

5. A reinforced joint assembly adapted to being installed between reconditioned ends of first and second join defining bones, said assembly comprising:

a first implant having an annular recess defined in a rear for receiving an annular sectioned end of the first bone to mount said first implant to the first bone;

a second implant having an annular recess defined in a rear for receiving an annular sectioned end of the second bone to mount said second implant to the second bone in opposing fashion to said first implant to define a joint zone therebetween;

said first implant having a first surface profile and said second implant having a second surface profile, each of said surface profiles including multiple peaks and valleys which are contoured so as to mate with each other, each of said surface profiles further including a soften plastic exterior;

first and second tear drop shaped cartilage portions arranged at a first and second locations between said first and second surface profiles, pluralities of shortened and bunched strands connecting said first and second cartilage portions to locations along at least one of said opposing first and second surface profiles; and said cartilage portions each establishing multiple wear surfaces on opposite sides thereof and permitted by said bunched strands a limited range of contact with each of said first and second implant surface profiles.

6. The join as described in claim 5, at least one of said softened plastic surface profiles further comprising a fluid lubricant grid pattern having crosswise extending and fluid retaining tracks.

7. The join assembly as described in claim 5, each of said implants further comprising a roughened inner surface for promoting bone marrow adhesion.

8. The join assembly as described in claim 5, each of said tear drop shaped cartilage portions further comprising a harder inner material around which is formed a softened outer coating.

* * * * *

UNITED STATES PATENT AND TRADEMARK OFFICE
CERTIFICATE OF CORRECTION

PATENT NO. : 8,764,837 B2  
APPLICATION NO. : 12/411149  
DATED : July 1, 2014  
INVENTOR(S) : Miguel A. Linares Page 1 of 1

It is certified that error appears in the above-identified patent and that said Letters Patent is hereby corrected as shown below:

In the Claims:

At column 9, claim number 5, line number 30, Delete "join", Insert --joint--.

At column 10, claim number 6, line number 22, Delete "join", Insert --joint--.

At column 10, claim number 7, line number 26, Delete "join", Insert --joint--.

At column 10, claim number 8, line number 29, Delete "join", Insert --joint--.

Signed and Sealed this  
Fifth Day of May, 2015

Michelle K. Lee  
*Director of the United States Patent and Trademark Office*